United States Patent [19]

Summers et al.

[11] Patent Number: 5,149,704
[45] Date of Patent: Sep. 22, 1992

[54] PLATELET ACTIVATING ANTAGONISTS

[75] Inventors: James B. Summers, Libertyville; Steven K. Davidsen, Mundelein; Douglas H. Steinman, Morton Grove; James G. Phillips, Antioch; Michael B. Martin, Waukegan; Denise E. Guinn, Grayslake, all of Ill.

[73] Assignee: Abbott Laboratories, Abbott Park, Ill.

[21] Appl. No.: 695,351

[22] Filed: May 3, 1991

[51] Int. Cl.$^5$ .................. C07D 417/04; A61K 31/44
[52] U.S. Cl. .................................. 514/342; 514/343; 514/336; 546/280; 546/281; 546/284
[58] Field of Search .................... 546/280; 514/342

[56] References Cited

U.S. PATENT DOCUMENTS 4,786,645 11/1988 Fabre et al. ..................... 514/333
4,940,709 7/1990 Shimazaki et al. ............... 514/253
4,948,795 8/1990 Mase et al. ....................... 514/252

FOREIGN PATENT DOCUMENTS 0279681 8/1988 European Pat. Off. .
0350145 1/1990 European Pat. Off. .

Primary Examiner—Jane T. Fan
Attorney, Agent, or Firm—Jerry F. Janssen

[57] ABSTRACT

Benzoylphenyl derivatives of 2-(3-pyridinyl)-3-alkyl-4-thiazolidinecarboxamide, 2-(3-pyridinyl)-thiazolid-4-ylacetamide, 2-(3-pyridinyl)-4-dithiolanecarboxamide or 2-(3-pyridinyl)dithiolan-4-yl]urea-group are potent inhibitors of PAF and are useful in the treatment of PAF-related disorders including anaphylactic shock, respiratory distress syndrome, acute inflammation, delayed cellular immunity, parturtition, fetal lung maturation, and cellular differentiation.

9 Claims, No Drawings

1

PLATELET ACTIVATING ANTAGONISTS

TECHNICAL FIELD

This invention relates to compounds having pharmacological activity, to compositions containing these compounds, and to a medical method of treatment employing the compounds and compositions. More particularly, this invention concerns certain pyridylthiazolidine, pyridyldioxalane, and pyridylpyrrolidine compounds and their salts which have platelet activating factor (PAF) antagonist activity, to pharmaceutical compositions containing these compounds, and to a method of treating PAF-mediated disorders.

BACKGROUND OF THE INVENTION

Platelet activating factor (PAF) is a phospholipid released from human and other animal cells and is an acetylglyceryl ether of phosphorylcholine as represented by the following formula:

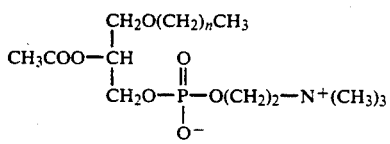

where n is 15 or 17.

PAF is physiologically active and causes contraction of the airway smooth muscle, increased vascular permeability, platelet aggregation, hypotension and the like. It is now recognized as a powerful mediator of inflammation and may play a physiological or pathobiologic role in a variety of clinical conditions, such as asthma and pulmonary dysfunction, acute inflammation, transplanted organ rejection, endotoxin and IgG-induced shock, thrombosis, cardiac anaphylaxis, gastrointestinal ulceration, allergic skin diseases, retinal and corneal diseases, chemically induced liver cirrhosis, and ovimplantation in pregnancy.

Several PAF antagonists have been reported (e.g., U.S. Pat. No. 4,948,795, European Patent Application EP 279681, and U.S. Pat. No. 4,786,645) but none have received wide acceptance. Therefore, there is a continuing need for the development of potent, orally active antagonists of PAF.

SUMMARY OF THE INVENTION

The present invention provides, in its principal aspect, compounds having PAF antagonist activity of the formula:

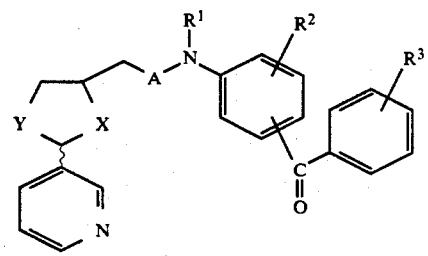

in which $R^1$ is hydrogen or alkyl of from one to six carbon atoms.

$R^2$ is one or more groups selected from hydrogen, halogen, or alkyl of from one to six carbon atoms.

$R^3$ is one or more groups selected from hydrogen, halogen, or alkoxy of from one to six carbon atoms.

A is absent or is $-N(R^4)C(O)-$ where $R^4$ is hydrogen or alkyl of from one to six carbon atoms.

X is sulfur or $>NR^5$ where $R^5$ is hydrogen, alkyl of from one to six carbon atoms, alkoyl of from one to six carbon atoms, $-C(O)NR^6R^7$ where $R^6$ and $R^7$ are independently selected from hydrogen and alkyl of from one to six carbon atoms, or $-C(O)OR^8$ where $R^8$ is an alkyl radical of from one to six carbon atoms.

The group Y is sulfur or methylene.

The pharmaceutically acceptable salts, and individual stereoisomers of compounds of structural formula I above, as well as mixtures thereof, are also contemplated as falling within the scope of the present invention.

In another aspect, the present invention provides pharmaceutical compositions useful for the treatment of PAF-mediated disorders comprising a therapeutically effective amount of a compound of formula I above in combination with a pharmaceutically acceptable carrier.

In yet another aspect, the present invention provides a method of inhibiting PAF activity by administering to a host mammal in need of such treatment a PAF-inhibiting effective amount of a compound of structure I above.

DETAILED DESCRIPTION AND PREFERRED EMBODIMENTS

In one embodiment of the present invention, compounds of the present invention are represented by Formula II:

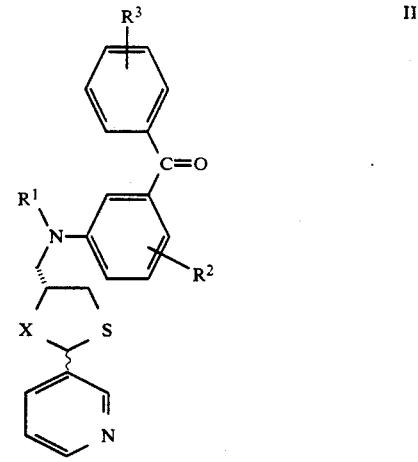

where X, $R^1$, $R^2$ and $R^3$ are defined as above.

Preferred compounds of Formula II are those in which $R^1$ and $R^2$ are hydrogen or alkyl of from one to six carbon atoms and $R^3$ is hydrogen or alkoxy from one to six carbon atoms. Particularly preferred compounds of Formula II are those in which $R^1$ are hydrogen or methyl, $R^2$ is hydrogen, and $R^3$ is hydrogen, 3,4-dimethoxy, 3,5-dimethoxy, or 3,4,5-trimethoxy.

In another embodiment, compounds of the present invention are represented by Formula III:

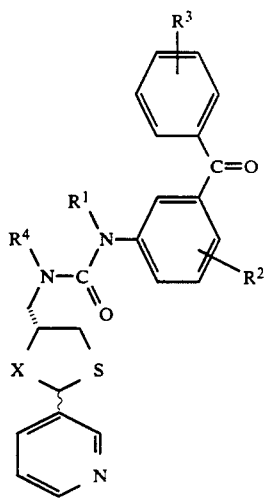

III where X, $R^1$, $R^2$, $R^3$, $R^4$ and $R^5$ are defined as above.

Preferred compounds of Formula III are those in which $R^1$ and $R^4$ are hydrogen or alkyl of from one to six carbon atoms, $R^2$ is hydrogen, $R^3$ is hydrogen or alkoxy of from one to six carbon atoms, $R^5$ is as defined above. Particularly preferred compounds of Formula III are those in which $R^1$ and $R^4$ are hydrogen or methyl, $R^2$ is hydrogen, $R^3$ is 3,4,5-trimethoxy, and $R^5$ is hydrogen.

Examples of compounds contemplated as falling within the scope of the present invention include, but are not necessarily limited to:

N-(3-benzoylphenyl) 2-(3-pyridinyl)thiazolid-4-ylmethylamine;

N-(4-benzoylphenyl) 2-(3-pyridinyl)thiazolid-4-ylmethylamine;

N-(3-benzoylphenyl) N-methyl 2-(3-pyridinyl)thiazolid-4-ylmethylamine;

N-(3-benzoylphenyl) [2-(3-pyridinyl)-3-methylthiazolid-4-yl]methylamine;

N-(3-benzoylphenyl) 2-(3-pyridinyl)-3-tert-butoxycarbonylthiazolid-4-ylmethylamine;

N-[3-(3,4,5-trimethoxybenzoylphenyl]2-(3-pyridinyl)-thiazolid-4-ylmethylamine

N-[3-(3,4,5-trimethoxybenzoylphenyl]-[2-(3-pyridinyl)-3-tert-butoxycarbonylthiazolid-4-yl]methylamine;

N-(4-phenoxyphenyl) 2-(3-pyridinyl)thiazolid-4-ylmethylamine;

N-[3-(3,4,5-trimethoxybenzoylphenyl]2-(3-pyridinyl)dithiolan-4-ylmethylamine;

N-(3-benzoylphenyl) 2-(3-pyridinyl)dithiolan-4-ylmethylamine;

N-[3-(3,4,5-trimethoxybenzoyl)phenyl][2-(3-pyridyl)-pyrrolidin-5-yl]methylamine

N-[2-(3-pyridinyl)thiazolid-4-ylmethyl]-N'-[3-(3,4,5-trimethoxybenzoyl)phenyl]urea;

N-[2-(3-pyridinyl)dithiolan-4-ylmethyl]N'-(3-benzoylphenyl)urea.

As used throughout this specification and the appended claims, the following terms have the meanings ascribed to them:

The term "alkoxy" as used herein refers to a lower alkyl group, as defined herein, which is bonded to the parent molecular moiety through an oxygen atom. Representative examples of alkoxy groups include methoxy, ethoxy, t-butoxy, and the like.

The term "alkoyl" as used herein refers to formyl and radicals of the structure —C(O)-alkyl in which the alkyl portion is a straight or branched alkyl group of from one to six carbon atoms. Representative examples of alkoyl groups include formyl, acetyl, propionyl, butyryl, isobutyryl, pivaloyl, and the like.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "carbamoyl" is used herein to mean —CONR$^6$R$^7$ wherein R$^6$ and R$^7$ are independently, hydrogen or a lower alkyl radical. Representative examples of carbamoyl groups, include carbamoyl, dimethylcarbamoyl, tert-butylcarbamoyl, methyl ethylcarbamoyl and the like.

The term "carboalkoxy" is used herein to mean —C(O)OR$^8$ wherein R$^8$ is an alkyl radical. Representative examples of carboalkoxy groups include carbomethoxy, carboethoxy, carboisopropoxy, carbobutoxy, carbosecbutoxy, carboiso-butoxy, carbotertbutoxy, and the like.

The terms "PAF-related disorders" and "PAF-mediated disorders" are used herein to mean disorders related to PAF or mediated by PAF, including asthma, shock, respiratory distress syndromes, gastric ulceration, transplant organ rejection, acute inflammation, psoriasis, allergic skin diseases, ischemia and reperfusion injury.

The term "pharmaceutically acceptable salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66: 1–19 (1977) which is incorporated herein by reference).

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage from may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 to about 100, more preferably of about 0.01 to about 20, and most preferably about 0.1 to about 10 mg of active compound per kilogram of body weight per day are administered orally to a mammalian patient. If desired, the effective daily dose may be divided into multiple doses for purposes of administration, e.g. two to four separate doses per day.

In general, the compounds of this invention are synthesized by reaction Schemes I though V as illustrated below. It should be understood that that X, Y, A, $R_1$, and $R_2$ as used herein correspond to the groups identified by Formula I.

The compounds of Formula (I–III) may be prepared using the reactions and techniques described in this section. The reactions are performed in a solvent appropriate to the reagents and materials employed and suitable for the transformation being effected. It is understood by those skilled in the art of organic synthesis that the functionality present on the heterocycle and other portions of the molecule must be consistent with the chemical transformation proposed. This will frequently necessitate judgement as to the order of synthetic steps, protecting groups required and deprotection conditions.

Scheme I

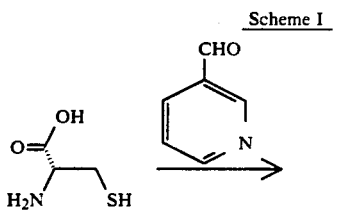

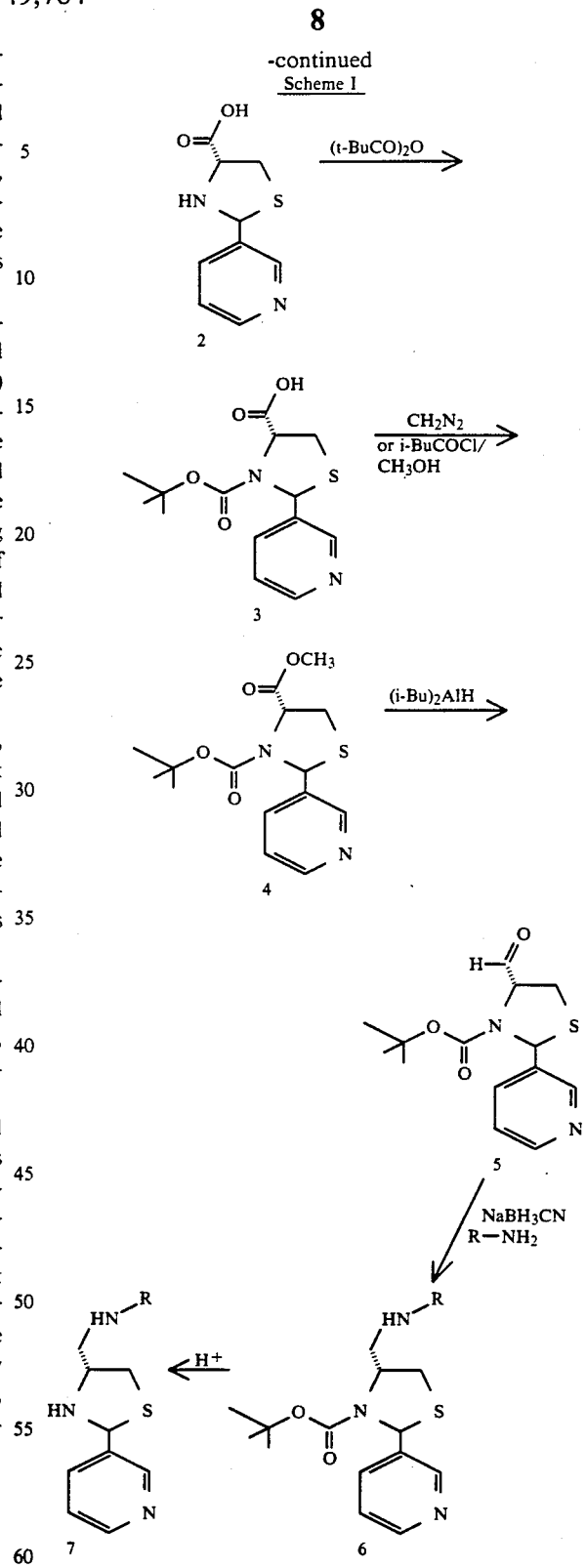

SCHEME I

According to the foregoing reaction Scheme I, L-cysteine (1) is condensed with 3-pyridine aldehyde to produce 2-(3-pyridinyl)-4-thiazolidinecarboxylic acid (2). The thiazolidine nitrogen may be protected with an appropriate group, preferably carbo-tert-butoxy (BOC)

with di-tert-butyl dicarbonate to afford 3. The protected acid is esterified to 4. The ester is reduced with an appropriate reducing agent, such as diisobutylaluminum hydride, to yield the aldehyde 5. The aldehyde undergoes a reductive amination with an amine and a reducing agent such as sodium cyanoborohydride to yield 6. The protecting group is removed under the appropriate conditions, as in the use of HCl to remove the BOC, and the amine 7 is obtained.

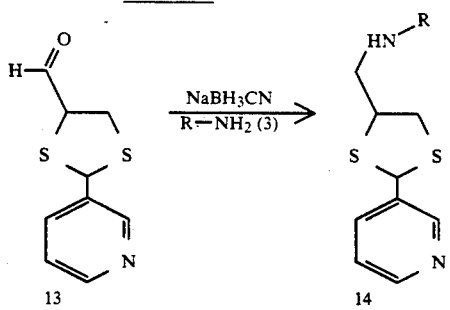

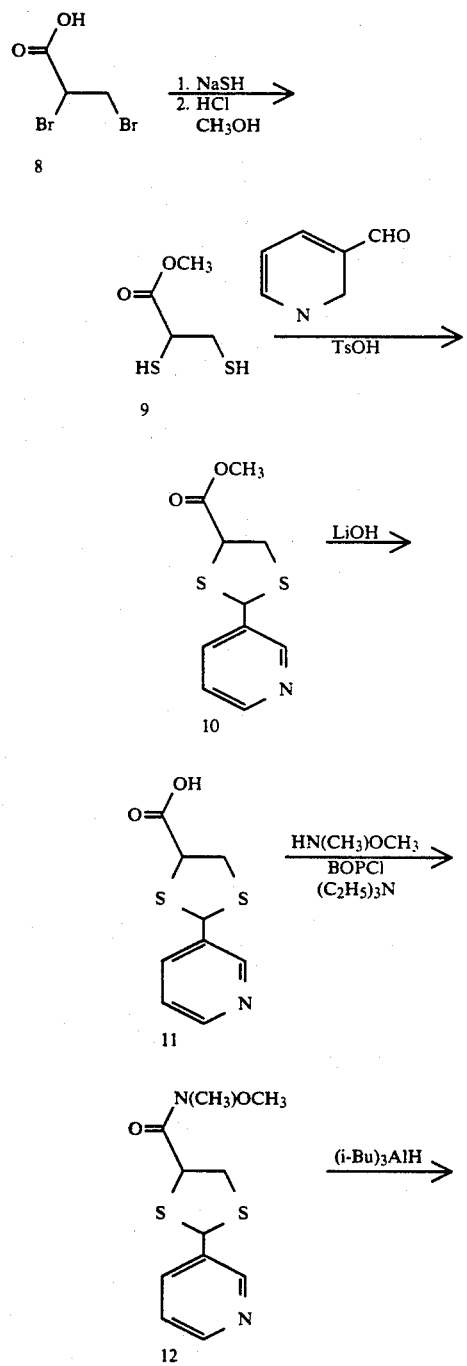

SCHEME II

According to the foregoing reaction Scheme II, 2,3-dibromopropionic acid (8) is treated with sodium bisulfide (NaSH) followed by esterification with HCl in methanol to give methyl 2,3-dimercaptopropionate (9). This dithiol (9) is condensed with 3-pyridine carboxaldehyde in the presence of an acid catalyst, preferably p-toluenesulfonic acid, to afford methyl 2-(3-pyridinyl)-4-dithiolanecarboxylate (10). The dithiolane ester is hydrolyzed to the corresponding acid (11) by treatment with aqueous base, preferably lithium hydroxide. 2-(3-Pyridinyl)-4-dithiolanecarboxylic acid (11) is then converted to N-methoxy-N-methyl 2-(3-pyridinyl)-4-dithiolanecarboxamide (12) with N-methoxy-N-methylamine in the presence of a coupling agent such as BOPCl (bis(2-oxo-3-oxazolidinyl)phosphinic chloride). The amide is reduced with an appropriate reducing agent, such as diisobutyl aluminum hydride, to give the aldehyde (13) which undergoes a reductive amination with an amine and a reducing agent such as sodium cyanoborohydride to 14.

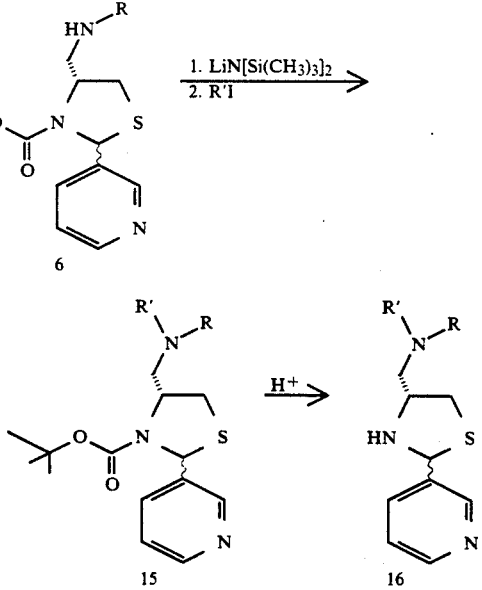

SCHEME III

According to the foregoing reaction Scheme III, amine 6 is first treated with a strong base, such as lithium hexamethyldislazide, followed by reaction with an alkyl halide to yield 15 which is then deprotected under acidic conditions to 16.
Scheme IV
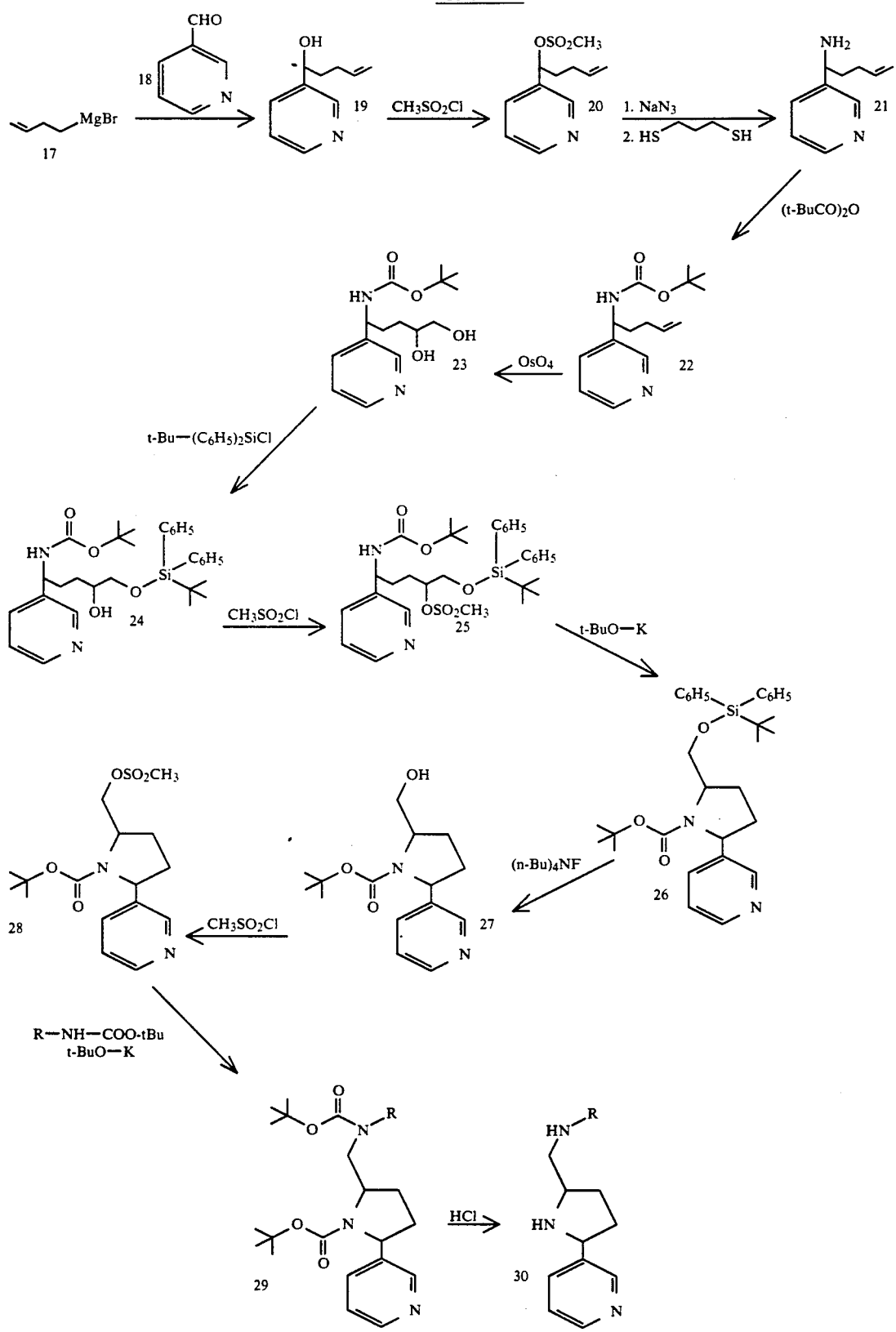

SCHEME IV

According to the foregoing reaction Scheme IV the Grignard reagent 4-bromomagnesium-1-butene (17) is reacted with an aldehyde (18), preferably pyridine-3-carboxaldehyde, to yield alcohol 19. The alcohol is sulfonated with an alkanesulfonate, preferably methanesulfonyl chloride, to yield the methanesulfonate 20. The methanesulfonate is reacted with sodium azide followed by 1,3-propanethiol and triethylamine to the aminopentene 21. The amine is protected with di-tert-butoxycarbonyl to give 22 which is hydroxylated to the diol 23. The diol is reacted with tert-butylchlorodiphenylsilane, followed by reaction with methanesulfonyl chloride to yield 25. The siloxypyrrolidine 26 is formed from 25 in the presence of a strong base, such as potassium tert-butoxide. The siloxy group is removed with tetra-n-butylammonium fluoride to give the alcohol 27 which is converted to the mesylate 28. The mesyl compound is displaced with an amine to give 29. The BOC groups are removed by treating the bis-protected amine with an acid, preferably hydrochloric acid, in dioxane to give amine 30.

PAF INHIBITORY ACTIVITY OF THE COMPOUNDS OF THE PRESENT INVENTION

The ability of representative compounds of the present invention to inhibit PAF activity was determined in an in vitro test using the following method.

Citrated whole rabbit blood was obtained from Pel-Freez (Rogers, AR). Rabbit platelets were prepared by centrifugation and washing. The platelets were lysed by freeze-thawing and sonication; platelet membranes were prepared by centrifugation and washing. Final membrane preparations were stored frozen in 10 mM Tris/5 mM $MgCl_2$/2 mM EDTA (TME buffer, pH 7.0) with 0.25M sucrose added for membrane stabilization.

The standard PAF receptor binding assay contained 10 μg platelet membrane protein, 0.6 nM [$^3$H]$C_{18}$-PAF (from Amersham or New England Nuclear; specific activity 120–180 Ci/mmol), with and without test compound, in "binding buffer" consisting of TME with 0.25% bovine serum albumin added (Sigma, RIA grade). The final volume of the assay was 100 μl. The assay was conducted in Millititre-GV TM (Millipore Corp.) filtration plates; incubation time was for 60 minutes at room temperature (22°–23° C.). "Specific binding" was operationally defined as the arithmetic difference between "total binding" of 0.6 nM [$^3$H]$C_{18}$-PAF (in the absence of added PAF) and "nonspecific binding" (in the presence of 1 μM PAF). After the prescribed incubation, platelet membranes were filtered under vacuum, and washed with 1 millilitre of "binding buffer". The filters were dried and removed. The bound radioactivity was quantitated with a Berthold TLC-Linear Analyzer model LB2842.

Dose-response curves of inhibition of specific [$^3$H]$C_{18}$-PAF binding by test compounds were conducted in triplicate, with at least four doses covering the active range. Experiments were repeated at least once. $IC_{50}$ values (concentration producing 50% inhibition) were determined by point-to-point evaluation. $K_i$ values

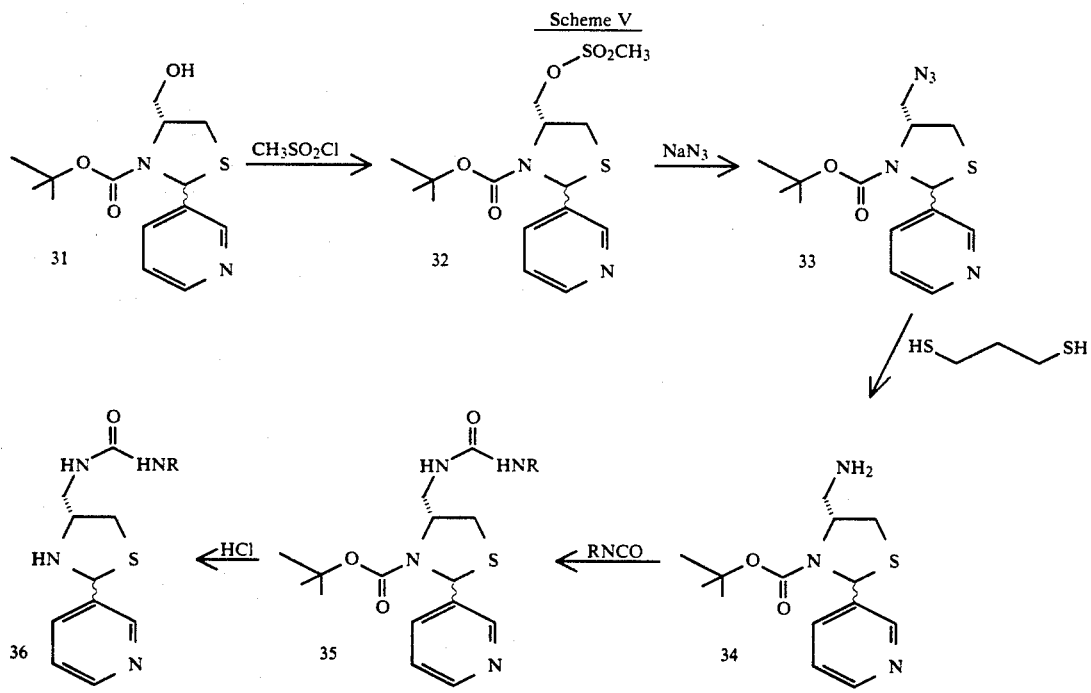

Scheme V

SCHEME V

According to the foregoing reaction Scheme V, 2-(3-pyridinyl)-3-tert-butoxycarbonylthiazolid-4-ylmethanol (31) is converted to methanesulfonate 32 which is reacted with sodium azide in dimethylformamide to the methylazide 33. The azide is reduced in the presence of 1,3-propanethiol to the amine 34. The amine is reacted with an isocyanate to the urea 35. The BOC protecting group is removed from the protected urea with acidic, preferably hydrochloric acid in dioxane, to yield give the urea 36.

of inhibitory binding constants were calculated according to the method of Cheng and Prusoff [*Biochem. Pharmacol.* 22 (1973) 3099–3108] whereby $$K_i = \frac{IC_{50}}{1 + ([[^3H]PAF]/K_d[^3H]PAF)}$$
$$= \frac{IC_{50}}{1 + (0.6 \text{ nM}/0.6 \text{ nM})}$$
$$= \frac{IC_{50}}{2}$$

The values of $K_i$ for representative compounds of the present invention appear in Table 1.

TABLE 1

PAF Receptor Binding Activity

| Example | $K_i$(nM) | Example | $K_i$(nM) |
|---------|-----------|---------|-----------|
| 1a      | 6,770     | 9       | 1,400     |
| 1b      | 13,000    | 10      | 900       |
| 2       | 10        | 11      | 160       |
| 3       | 8,700     | 12      | 3,400     |
| 4       | 23        | 13 (cis)| 2,300     |
| 5       | 38        | 13 (trans)| 8,700   |
| 6       | 430       | 14      | 110       |
| 7       | 1,200     | 15      | 150       |
| 8       | 190       | 16      | 750       |

The foregoing may be better understood from the following examples, which are presented for the purpose of illustration and not intended to limit the scope of the inventive concept.

EXAMPLE 1

Preparation of N-[3-(3,4,5-trimethoxybenzoylphenyl]-[2-(3-pyridinyl)-3-tert-butoxycarbonylthiazolid-4-yl]methylamine Step 1. Preparation of 2-(3-pyridinyl)-4-thiazolidine carboxylic acid Cysteine (24.2 g, 0.2 mole) and 3-pyridine carboxaldehyde (21.4 g, 0.2 mmole) were suspended in 60% aqueous ethanol (400 mL) and the mixture was heated at 100° C. for 5 hours. The reaction mixture was then cooled and most of the solvent was removed in vacuo. The resulting slurry was filtered and washed with ethanol. This material was dried overnight in vacuo at 50° C. to afford the thiazolidine acid (34 g, 81%).

Step 2. Preparation of 2-(3-pyridinyl)-3-tert-butoxycarbonyl-4-thiazolidinecarboxylic acid To a slurry of 2-(3-pyridinyl)-4-thiazolidinecarboxylic acid (7.0 g; 33.3 mmol.), prepared as in Step 1, in dioxane (40 mL) at 0° C. was added aqueous NaOH (60 mL, 1M), followed by a solution of di-tert-butyl dicarbonate (1.5 eq; 10.9 g) and dioxane (20 mL) in one portion. The resulting yellowish solution was warmed to room temperature stirred for 19 hours. The resulting solution was concentrated on a rotary evaporator and the resulting residue was partitioned between ethyl acetate (100 mL) and water (100 mL). The aqueous phase was washed with ethyl acetate and then acidified to a pH of 4 with aqueous hydrochloric acid at 0° C. This solution was then extracted with ethyl acetate and dried over magnesium sulfate to yield 2-(3-pyridinyl)-3-tert-butoxycarbonyl-4-thiazolidinecarboxylic acid (8.27 g, 80% yield) as a white solid.

Step 3. Preparation of methyl 2-(3-pyridinyl)-3-(tert-butoxycarbonyl)-4-thiazolidinecarboxylate To a solution of 2-(3-pyridinyl)-3-(tert-butoxycarbonyl)-4-thiazolidinecarboxylic acid prepared as in step 2 (10 g) in dry tetrahydrofuran (THF, 160 mL; 0.2M) under nitrogen at 0° C. with stirring was added N-methylmorpholine (3.9 mL, 1.1 eq.) followed by isobutylchloroformate (4.2 mL, 1.0 eq.). The resulting reddish mixture was stirred for 15 minutes, followed by the addition of methanol (10 mL). The reaction mixture was warmed to room temperature and allowed to stir for 16 hours. The resulting mixture was concentrated and partitioned between ethyl acetate and saturated sodium bicarbonate. The organic layer was washed with brine and dried over magnesium sulfate. Filtration and removal of the solvent gave the title compound as an orange oil. The oil was further purified by flash chromatography on silica gel (eluting with 1:1 hexanes:ethyl acetate).

Step 4. Preparation of 2-(3-pyridinyl)-3-(tert-butoxycarbonyl)-4-thiazolidinecarboxaldehyde Methyl 2-(3-pyridinyl)-3-(tert-butoxycarbonyl)-4-thiazolidinecarboxylate (43 mmol, prepared as described in Step 3 above) in methylene chloride under nitrogen at −70° C. with stirring was mixed with a solution of di-isobutylaluminum hydride (Dibal, 120 mL of 1M, 3 eq.) in methylene chloride and stirred for 2 hours at −70° C. After this time, saturated sodium chloride was added and the mixture warmed to room temperature with stirring for 30 minutes. Aqueous sodium hydroxide was then added, the mixture agitated and the layers separated. The aqueous phase was extracted with methylene chloride and the organic layers washed with aqueous sodium hydroxide and brine. Filtration, followed by concentration gave an orange oil which was purified by flash chromatography on silica gel (45:55 hexanes:ethyl acetate) to yield 2-(3-pyridinyl)-3-(tert-butoxycarbonyl)-4-thiazolidinecarboxaldehyde (9.18 g, 72%) as a yellow oil.

Step 5. Preparation of N-tertbutylcarbonyl-3-iodoaniline

3-Iodoaniline (25 g, 114.13 mmol) and di-tert-butyldicarbonate (24.89 g) were mixed in methylene chloride at room temperature with stirring. Dimethylaminopyridine (50 mg) was then added and the mixture stirred at room temperature overnight. The mixture was poured into 0.1N HCl and the organic phase was separated, dried over sodium sulfate and the solvent evaporated. The material was purified by flash chromatography over silica gel (eluting with 6:1 hexane:ethyl acetate) and the resulting residue recrystallized from ethyl acetate/hexane to yield 26.11 g (75%) of N-tert-butylcarbonyl-3-iodoaniline as a white solid.

Step 6. Preparation of N-tertbutylcarbonyl-3-tributyltin-aniline

N-tert-butylcarbonyl-3-iodoaniline (28.2 g, 92.5 mmoL), prepared as described above, hexabutylditin (46.7 mL, 92.5 mmol), and tetrakis(triphenylphosphine)-palladium (2.13 g) in toluene were mixed at 80° C. over a 48 hour period. The mixture was shaken with an ethyl acetate-water mixture, the organic layer separated and the solvent evaporated. Hexane was added to the residue and the mixture was filtered through Celite. The filtrate was evaporated to 40 mL and the residue purified by flash chromatography on silica gel (eluting with 19:1 hexane:ethyl acetate) to yield N-tert-butylcarbonyl-3-tributyltin-aniline (22.6 g, 51%).

Step 7. Preparation of N-tertbutylcarbonyl-3-(3,4,5-trimethoxybenzoyl)aniline

N-tert-butylcarbonyl-3-tributyltine-aniline (18.6 g, 38.58 mmol) and 3,4,5-trimethoxybenzoyl chloride (8.81 g, 38.19 mmol) were added to benzyl tetrakis(triphenylphosphine)palladium chloride (155 mg) in tetrahydrofuran with stirring and heated to 65° C. for 16 hours. Ethyl acetate (250 mL) was added and the organic layer separated and dried over sodium sulfate. The material was purifed by flash chromatography over silica gel to yield 7.12 g (49.68%) N-tert-butylcarbonyl-3-(3,4,5-trimethoxybenzoyl)aniline.

Step 8. Preparation of 3-(3,4,5-trimethoxybenzoyl)aniline

N-tert-butylcarbonyl-3-(3,4,5-trimethoxybenzoyl)aniline (7.10 g, 18.92 mmol), prepared as described above, was dissolved in acetic acid (125 mL, 1.4N) at room temperature. A solution of hydrochloric acid/acetic acid (20 mL) was added and the mixture allowed to stir for 45 minutes. Diethylether (800 mL) was added and the resulting precipitate filtered and dried to yield 3-(3,4,5-trimethoxybenzoyl)aniline hydrochloride (5.24 g, 85.7%) as a tan solid.

Step 9. Preparation of N-[3-(3,4,5-trimethoxybenzoylphenyl]2-(3-pyridinyl)-3-tert-butoxycarbonylthiazolid-4-ylmethylamine To a solution of 2-(3-pyridinyl)-3-(tert-butoxycarbonyl)-4-thiazolidinecarboxaldehyde (183 mg, 0.62 mmol, prepared as in step 4, above) was added 3-(3,4,5-trimethoxybenzoyl)aniline hydrochloride (241 mg, 1.2 eq., prepared as in Step 8, above) followed by sodium cyanoborohydride (98 mg, 2.5 eq.). The resulting reaction mixture was stirred at room temperature for over 16 hours. The mixture was then concentrated and partitioned between ethyl acetate and saturated sodium bicarbonate. The organic layers were washed with saturated sodium bicarbonate and dried over magnesium sulfate. Filtration, followed by concentration, and purification by flash chromatography on silica gel gave (eluting with 1:1 hexanes:ethyl acetate) 214 mg of the title compound as a yellow oil.

EXAMPLE 2

Preparation of N-[3-(3,4,5-trimethoxybenzoylphenyl]2-(3-pyridinyl)-thiazolid-4-ylmethylamine trihydrochloride To a solution of N-[3-(3,4,5-trimethoxybenzoylphenyl]2-(3-pyridinyl)-3-tert-butoxycarbonylthiazolid-4-ylmethylamine (214 mg, prepared as described in Example 1) in a minimum amount of dioxane was added hydrochloric acid in dioxane (8 mL of 4M) and the resulting solution was stirred at room temperature for 3 hours. The resulting solution was then concentrated and partitioned between water and ethyl acetate. The pH of aqueous phase was adjusted to pH 8 with sodium bicarbonate, followed by extraction with methylene chloride. The organic solution was dried over magnesium sulfate, filtered and concentrated to a yellow oil. The material was further purified by flash chromatography on silica gel (eluting with 1:9 hexanes:ethyl acetate) to yield 94 mg of a yellow oil. The product was dissolved in a minimum amount of dioxane, cooled to 0° C. and a solution of hydrochloric acid in dioxane (4M) added. This solution was allowed to stir for 15 minutes and was then concentrated to give the hydrochloride salt as a white solid. NMR (CDCl$_3$, 300 MHz): δ2.90 (t, 1H, J=10.0), 2.96 (dd, 1H, J=6.0, 10.0), 3.29–3.42 (c, 2H), 3.58–3.79 (c, 2H), 3.88 (s, 6H), 3.93 (s, 3H), 4.24–4.38 (c, 1H), 5.61 (bs, 1H), 6.87 (m, 1H), 7.08 (m, 2H), 7.23–7.34 (c, 3H), 7.82 (tt, 1H, J=1.0, 9.0), 8.56 (m, 1H), 8.74 (d, 1H, J=2.0). IR (CDCl$_3$): 1725, 1600, 1580, 1330, 1125. Mass Spectrum (DCI/NH$_3$): 466 (M+H)$^+$.

EXAMPLE 3

Preparation of N-(3-benzoylphenyl)2-(3-pyridinyl)-3-tert-butoxycarbonylthiazolid-4-ylmethylamine N-(3-benzoylphenyl)2-(3-pyridinyl)-3-tert-butoxycarbonylthiazolid-4-ylmethylamine was prepared using the method of Example 1, except 3-benzoylaniline hydrochloride was used instead of 3-(3,4,5-trimethoxybenzoyl)aniline. NMR (CDCl$_3$, 300 MHz): δ1.28 (bs, 9H), 2.98 (dd, 1H, J=1.0, 12.0), 3.36 (dd, 1H, J=7.0, 12.0), 3.50 (m, 1H), 3.65 (m, 1H), 4.80 (m, 1H), 6.01 (bs, 1H), 6.92 (m, 1H), 7.08 (m, 2H), 7.20–7.36 (c, 4H, 7.43–7.49 (c, 2H), 7.56 (m, 1H), 7.81 (m, 2H), 8.52 (dd, 1H, J=6.0). Mass Spectrum (DCI/NH$_3$): 476 (M+H)$^+$.

EXAMPLE 4

Preparation of N-(3-benzoylphenyl)2-(3-pyridinyl)thiazolid-4-ylmethylamine

N-(3-benzoylphenyl)2-(3-pyridinyl)thiazolid-4-ylmethylamine was prepared using the method of Example 2, except 3-benzoylaniline was used instead of 3-(3,4,5-trimethoxybenzoyl)aniline. NMR (CDCl$_3$, 300 MHz): δ2.84–2.96 (c, 1H), 3.20–3.46 (c, 3H), 3.56–3.69 (c, 1.2H), 3.96 (m, 0.8H, J=6.0), 5.77 (d, 0.2H, J=6.0), 6.56 (bt, 0.2H, J=8.5), 6.71 (m, 0.8H), 6.86 (m, 1H), 7.06–7.12 (c, 2H), 7.22–7.33 (c, 2H), 7.46 (dt, 2H, J=1.0, 8.0), 7.58 (t, 1H, J=7.0), 7.76–7.87 (c, 3H), 8.55 (m, 1H), 8.72 (d, 0.2H, J=1.5), 8.74 (d, 0.8H, J=1.5). IR (CDCl$_3$): 1650, 1595, 1575. Mass Spectrum (DCI/NH$_3$): 376 (M+H)$^+$.

EXAMPLE 5

Preparation of N-(3-benzoylphenyl)2-(3-pyridinyl)thiazolid-4-ylmethylamine trihydrochloride N-(3-benzoylphenyl)2-(3-pyridinyl)thiazolid-4-ylmethylamine trihydrochloride was prepared using the method of Example 2. The product was taken up in a minimum amount of dioxane cooled to 0° C. and a solution of hydrochloric acid in dioxane (4M) was added and this solution stirred over 15 minutes and then concentrated to a white solid. Mass Spectrum (DCI/NH$_3$): 376 (M+H)$^+$.

EXAMPLE 6

Preparation of N-(2-benzoylphenyl)2-(3-pyridinyl)thiazolid-4-ylmethylamine

N-(2-benzoylphenyl)2-(3-pyridinyl)thiazolid-4-ylmethylamine was prepared using the method of Example 2 except 2-benzoylaniline was used instead of 3-(3,4,5- trimethoxybenzoyl)aniline. Mass Spectrum (DCI/NH$_3$): 376 (M+H)+.

EXAMPLE 7

Preparation of N-(4-benzoylphenyl)2-(3-pyridinyl)thiazolid-4-ylmethylamine

N-(4-benzoylphenyl)2-(3-pyridinyl)thiazolid-4-ylmethylamine was prepared using the method of Example 2, except 4-benzoylaniline was used instead of 3-(3,4,5-trimethoxybenzoyl)aniline. Mass Spectrum (DCI/NH$_3$): 376 (M+H)+, 228, 166.

EXAMPLE 8

Preparation of N-(4-phenoxyphenyl)2-(3-pyridinyl)thiazolid-4-ylmethylamine

N-(4-phenoxyphenyl)2-(3-pyridinyl)thiazolid-4-ylmethylamine was prepared using the method of Example 1, except 4-phenoxylaniline was used instead of 3-(3,4,5-trimethoxybenzoyl)aniline. NMR (CDCl$_3$, 300 MHz): δ2.92 (m, 1H), 3.15–3.39 (c, 2H), 3.51–3.69 (c, 1H), 3.95 (m, 1H), 5.62 (d, 1H, J=9.0), 6.65 (t, 2H, J=8.5), 6.84–7.05 (c, 4H), 7.21–7.36 (c, 4H), 7.82 (t, 1H, J=8.0), 8.56 (t, 1H, J=6.5), 8.75 (s, 1H). Mass Spectrum (DCI/NH$_3$): 364 (M+H)+.

EXAMPLE 9

Preparation of N-(3-benzoylphenyl)[2-(3-pyridinyl)-3-methylthiazolid-4-yl]methylamine dihydrochloride

Step 1. Preparation of ethyl 2-(3-pyridyl)-3-methyl-4-thiazolidinecarboxylate Ethyl 2-(3-pyridyl)-4-thiazolidinecarboxylate (2.0 g, 1.0 eq.) and aqueous formaldehyde was dissolved in acetonitrile and stirred for 30 minutes. Sodium cyanoborohydride (0.79 g, 1.5 eq.) was added and the reaction taken to pH 3 with glacial acetic acid. After another 30 minutes, more acetic acid was added. The reaction was stirred overnight at room temperature and quenched with water and poured into saturated sodium bicarbonate. The aqueous phase was extracted with ethyl acetate and the combined organic layers washed with brine, dried over magnesium sulfate, filtered and concentrated to a yellow oil. The oil was purified by flash chromatography on silica gel (eluted with 3:1 ethyl acetate: hexanes) to give 1.0 g of the title compound (48%) yield.

Step 2. Preparation of N-(3-benzoylphenyl)2-(3-pyridinyl)-3-tert-butoxycarbonylthiazolid-4-ylmethylamine N-(3-benzoylphenyl)2-(3-pyridinyl)-3-tert-butoxycarbonylthiazolid-4-ylmethylamine was prepared as described in Example 1 except ethyl 2-(3-pyridyl)-3-methyl-4-thiazolidinecarboxylate (prepared as described above) was used instead of methyl 2-(3-pyridinyl)-3-(tert-butoxycarbonyl)-4-thiazolidinecarboxylate.

EXAMPLE 10

Preparation of N-[3-(3,4,5-trimethoxybenzoylphenyl]]2-(3-pyridinyl)dithiolan-4-ylmethylamine dihydrochloride

Step 1. Preparation of methyl 2,3-dimercaptopropionate

To a flame dried 1 liter 3-neck fask was added 30 g (1.25 mol, 5.8 eq) of sodium spheres (rinsed with hexanes). The flask was equipped with an addition funnel and a reflux condenser. Anhydrous methanol (400 mL) was added to the sodium metal via the addition funnel in a dropwise fashion at such a rate so as to maintain a gentle reflux throughout the addition. After approximately 45 minutes, the reaction was cooled to 0° C. and saturated with gaseous H$_2$S for 1 hr. During the course of the addition excess H$_2$S was neutralized by bubbling the bleed line through a trap containing a 10% solution of aqueous sodium hydroxide. A solution of 50.0 g (0.22 mol, 1 eq.) 2,3-dibromopropionic acid dissolved in 100 ml of methanol was added to the reaction mixture via the addition funnel at a rapid drip rate. The solution was allowed to warm to room temperature and was stirred an additional 18 hr.

The reaction was then acidified to pH 2 by initial dropwise addition of 100 mL of saturated methanolic HCl (H$_2$S evolution observed) followed by bubbling gaseous HCl into the reaction mixture until the desired pH was obtained. At this point, a thick white precipitate was present. The solution was allowed to stir for an additional 4 hours and then concentrated on a rotoevaporator to remove the methanol. The resulting pasty residue was partitioned between 300 mL of water and 300 mL of ethyl ether. The aqueous phase was extracted with ethyl ether (2×) and the combined organic extracts washed once with brine and dried over magnesium sulfate. The drying agent was filtered off and the filtrate concentrated in vacuo. Yield: 28.5 g, 86.5% of a light yellow oil.

Step 2. Preparation of methyl 2-(3-pyridinyl)-4-dithiolanecarboxylate

To a 3-neck round bottomed flask equipped with a Dean Stark trap and a constant rate addition funnel was added 7.05 g (65.7 mmol, 1.0 eq.) of 3-pyridinealdehyde and 15.0 g (78.9 mmol, 1.2 eq.) p-toluenesulfonic acid in 350 mL of toluene and 40 ml 1-butanol. The solution was heated to reflux, whereupon 10.0 g (65.7 mmol, 1 eq.) of the material prepared as in step 1, above, in 30 mL toluene was added dropwise over ninety minutes to the refluxing reaction mixture via the addition funnel. The reaction was allowed to reflux overnight and the following day cooled to room temperature and concentrated in vacuo. The residue was partitioned between saturated aqueous sodium bicarbonate and ethyl acetate (requires agitation for >30 min). The aqueous phase was extracted one more time with ethyl acetate. The combined organic extracts were then washed successively with saturated aqueous sodium bisulfite (×2), 1M aqueous sodium hydroxide (×2), and saturated aqueous brine (×1), dried over sodium sulfate, filtered and concentrated in vacuo to afford 18.57 g (117% crude yield) of a brown oil. TLC showed predominantly desired material along with some nicotinaldehyde and a much less polar impurity. The oil was purified by flash chromatography (SiO$_2$, 80:20 hexanes:ethyl acetate). The desired dithiolane was isolated in fractions 85–195 as 8.03 g (50.6% yield) of an orange oil. NMR δ(CDCl$_3$) 3.45 (dd, 0.5H), 3.6 (dd, 0.5H), 3.65 (dd, 0.5H), 3.7 (dd, 0.5H), 3.8 (s, 1.5H), 3.82 (s, 1.5H), 4.5 (t, 0.5H), 4.65 (t, 0.5H), 5.65 (s, 0.5H), 5.75 (s, 0.5H), 7.3 (dd, 1H), 7.95 (ddt, 1H), 8.5 (td, 1H), 8.7 (dd, 1H).

Step 3. Preparation of 2-(3-pyridinyl)-4-dithiolanecarboxylic acid

Dithiolane ester (2 g, 8.3 mmol, 1 eq.), prepared as in step 2 above, was dissolved in a 3:1 (v/v) solution of tetrahydrofuran and water and 432 mg of lithium hydroxide hydrate (10 mmol, 1.2 eq.) added in one portion. The reaction immediately assumed an orange color. The reaction was concentrated in vacuo to remove tetrahydrofuran and the resulting aqueous solution extracted with ether to remove any impurities. The aqueous phase was acidified to pH=4 with 1N aqueous hydrochloric acid and concentrated in vacuo. The resulting oily residue was then suspended in tetrahydrofuran and ethanol and filtered. The filtrate was concentrated in vacuo and chased two times with toluene to afford 1.6 g (85% yield) of a yellow solid.

Step 4. Preparation of N-methoxy-N-methyl 2-(3-pyridinyl)-4-dithiolanecarboxamide To a solution of 2-(3-pyridinyl)-4-dithiolanecarboxylic acid (781 mg, 3.4 mmol, 1 eq.), prepared as described in step 3, above, in 30 mL of dichloromethane was added N-methoxy-N-methylamine hydrochloride (363 mg, 3.7 mmol, 1.1 eq.) followed by bis(2-oxo-3-oxazolidinyl)-phosphinic chloride (961 mg, 3.7 mmol, 1.1 eq.) and triethylamine (1.7 mL, 12.2 mmol, 3.5 eq.). The reaction was allowed to stir at room temperature under nitrogen overnight. The following day the reaction was diluted with dichloromethane and washed with saturated aqueous sodium bicarbonate (1×), saturated aqueous NaCl(1×), dried over sodium sulfate, filtered and concentrated in vacuo. The residue was purified by flash chromatography on silica gel (eluting with 35:65 hexanes:ethyl acetate) to afford 426 mg (44% yield) of the product as a yellow oil.

Step 5. Preparation of 2-(3-pyridinyl)-3-(tert-butoxycarbonyl)-4-dithiolanecarboxaldehyde A solution of N-methoxy-N-methyl 2-(3-pyridinyl)-4-dithiolanecarboxamide (302 mg, 1.1 mmol, prepared as described above) was cooled to −78° C. and di-isobutyl aluminum hydride (DIBAL, 3.0 eq.) was added dropwise and the reaction mixture stirred for 2 hours. The reaction was quenched by addition of sodium chloride and the resulting mixture partitioned between sodium hydroxide and ethyl acetate. The organic layer was washed with brine, dried over sodium sulfate, filtered, and the solvent removed in vacuo to yield 209 mg (90%) yield of the title compound.

Step 6. Preparation of N-[3-(3,4,5-trimethoxybenzoylphenyl]2-(3-pyridinyl)dithiolan-4-ylmethylamine dihydrochloride The aldehyde (109 mg, 0.5 mmol, prepared as above in Step 5) was dissolved in methanol and reacted with 3-(3,4,5-trimethoxybenzoyl) aniline (81 mg, 1.3 mmol, prepared as described in Example 1, step 8) in the presence of sodium cyanoborohydride (81 mg, 2.5 eq., 1.3 mmol). The pH of the solution was adjusted to pH 3 with acetic acid and the reaction mixture stirred overnight under nitrogen. The reaction contents were concentrated in vacuo and the residue partitioned between sodium bicarbonate and ethyl acetate. The organic layers were washed with brine and dried over sodium sulfate, and filtered to yield 390 mg of a yellow oily solid. The material was further purified by flash chromatography over silica gel (eluting with 60:40 hexanes:ethyl acetate). The amine was converted to the dihydrochloride salt by stirring in 4M hydrochloric acid and dioxane for 2 hours. The reaction was concentrated in vacuo and chased with methylene chloride to yield the title compound. NMR (CDCl$_3$, 300 MHz): δ3.3–3.6 (c, 3H), 3.7 (dd, 1H, J=8 Hz), 4.1–4.2 (c, 0.5H), 4.25–4.35 (c, 0.5H), 5.63 (s, 0.5H), 5.67 (s, 0.5H), 6.87 (m, 1H), 7.1 (m, 2H), 7.25–7.35 (c, 3H), 7.4–7.5 (c, 2H), 7.55 (m, 1H), 7.8 (m, 2H), 7.9 (ddt, 1H, J=2,9,15 Hz), 8.5 (td, 1H, J=2, 5 Hz), 8.7 (dd, 1H, J=2,8 Hz). IR (CDCl$_3$): 3300 (br), 1660, 1600, 1590, 1280.

Mass Spectrum (DCI/NH$_3$): 393 (M+1)+, 215, 182.

EXAMPLE 11

Preparation of N-(3-benzoylphenyl)2-(3-pyridinyl)dithiolan-4-ylmethylamine

N-(3-benzoylphenyl)2-(3-pyuridinyl)dithiolan-4-ylmethylamine was prepared using the procedure of Example 10, except 3-benzoylaniline was used instead of 3-(3,4,5-trimethoxybenzoyl)aniline. NMR (CDCl$_3$, 300 MHz): δ3.35 (dd, 0.5H, J=5, 12 Hz), 3.45 (dd, 0.5H, J=2, 5 Hz), 3.55 (dd, 0.5H, J=5, 12 Hz), 3.8 (m, 0.5H), 3.87 (s, 6H), 3.95 (s, 3H), 4.1–4.2 (c, 2H), 4.27–4.35 (c, 2H), 5.65 (s, 0.5H), 5.67 (s, 0.5H), 6.85 (m, 0.5H), 6.9 (m, 0.5H), 7.1 (s, 2H), 7.1 (m, 0.5H), 7.25 (s, 2H), 7.27 (m, 0.5H), 7.89 (ddd, 0.5H, J=3, 3, 8 Hz), 7.95 (ddd, 0.5H, J=3, 3, 9 Hz), 8.53 (m, 1H), 8.68 (br d, 0.5H, J=3 Hz), 8.72 (br d, 0.5H, J=3 Hz). IR (CDCl$_3$): 2900 (br), 1650 (weak), 1580, 1460, 1420, 1340, 1130. Mass Spectrum (FAB): 483(M+1)+

EXAMPLE 12

Preparation of N-(3-benzoylphenyl) N-methyl 2-(3-pyridinyl)thiazolid-4-ylmethylamine trihydrochloride

Step 1. Preparation of N-(3-benzoylphenyl)2-(3-pyridinyl)-3-tert-butoxycarbonylthiazolid-4-ylmethylamine To a solution of N-(3-benzoylphenyl)2-(3-pyridinyl)-3-tert-butoxycarbonylthiazolid-4-ylmethylamine (201 mg, 0.42 mmol., prepared as described in Example 3) and dry tetrahydrofuran at 0° C. with stirring under nitrogen was added lithium bis(trimethylsilyl)amide followed by addition of methyl iodide (32 μL, 1.3 eq). The resulting mixture was stirred for 3 hours at 0° C. The solution was partitioned between ethyl acetate and sodium bicarbonate, the organic layer dried over magnesium sulfate, filtered, and evaporated to give 259 mg of the title compound as an orange oil. The compound was further purified by flash chromatography on silica gel (eluting with 1:3 hexanes:ethyl acetate).

Step 2. Preparation of N-(3-benzoylphenyl) N-methyl 2-(3-pyridinyl)thiazolid-4-ylmethylamine trihydrochloride To a solution of N-(3-benzoylphenyl)2-(3-pyridinyl)-3-tert-butoxy-carbonylthiazolid-4-ylmethylamine (57 mg, prepared as in Step 1) in dioxane at room temperature with stirring was added hydrochloric acid in dioxane (5 mL, 4M) and the resulting solution stirred for over 18 hours. The reaction mixture was concentrated, partitioned between methylene chloride and saturated aqueous sodium carbonate. The aqueous phase was extracted with methylene chloride and the organic layers dried over magnesium sulfate, filtered and dried. The resulting red oil was purified by flash chromatography on silica gel eluting with ethyl acetate. This material was converted to the dihydrochloride using 4M hydrochloric acid and dioxane to yield 15 mg of the title compound as an orange solid. NMR (CDCl$_3$, 300 MHz): δ2.91 (m, 1H), 3.08 (s, 1.5H), 3.09 (s, 1.5H), 3.20 (dd, 1H; J=6.0, 10.0), 3.54–3.60 (c, 2.5H), 3.91 (m, 0.5H), 5.58 (s, 0.5H), 5.70 (s, 0.5H), 6.96–7.09 (c, 1H), 7.19–7.36 (c, 5H), 7.48 (m, 2H), 7.56 (m, 1H), 7.81 (m, 2H), 8.52 (dd, 0.5H, J=1.0, 6.0), 8.57 (dd, 0.5H, J=1.0, 6.0), 8.71 (d, 0.5H, J=1.0), 8.73 (d, 0.5H, J=1.0). Mass Spectrum (DCI/NH$_3$): 390 (M+H)$^+$, 107.

EXAMPLE 13

Preparation of
N-[3-(3,4,5-trimethoxybenzoyl)phenyl][2-(3-pyridyl)-pyrrolidin-5-yl]methylamine Step 1. Preparation of 1-(3-Pyridyl)-pen-4-en-1-ol Grignard reagent 4-but-1-ene magnesium bromide was conventionally prepared from 4-bromo-1-butene (50 g, 0.3703 mol. Aldrich) and reacted with pyridine-3-carboxaldehyde (38.54 g, 0.359 mol.) via a dropwise addition of the Grignard solution. The resulting mixture was allowed to slowly warm to room temperature and stirred overnight. The reaction was quenched by addition of saturated aqueous ammonium chloride and the layers separated. The organic layers were combined and dried over magnesium sulfate, filtered, and the filtrate concentrated via rotary evaporation to an orange oil. This material was purified by chromatography on silica gel (eluting with 3:7 ethyl acetate/hexanes) to yield 25.97 gram (43%) of 1-(3-pyridyl)-pen-4-en-1-ol.

Step 2. Preparation of 1-(3-pyridyl)-pen-4-en-1-yl methanesulfonate 1-(3-pyridyl)-pent-4-en-1-ol (24.96 g, 0.1529 mol., prepared as in step 1 above) in methylene chloride was stirred under nitrogen and triethylamine (0.1827 mol) added via a syringe. Methanesulfonyl chloride (19.27 g, 0.168 mol.) in methylene chloride was added to the mixture dropwise over a period of 1 hour. The reaction was quenched 30 minutes after the complete addition of the methanesulfonyl chloride with saturated aqueous ammonium chloride. The resulting layers were separated and the organic layers washed with sodium bicarbonate and brine. The organic extract was concentrated to a yellow oil (36.4 g, 99% yield).

Step 3. Preparation of 1-(3-Pyridyl)-1-aminopent-4-ene 1-(3-pyridyl)-pent-4-en-1-yl methanesulfonate (36.4 g, 0.1508 mol.) in ethanol was reacted with a solution of sodium azide (0.1597 mol) in ethanol. The reaction mixture was stirred for 2 hours at room temperature, followed by rapid addition of 1,3-propanedithiol (0.2778 mol.) and triethylamine (45 mL, 0.3194 mol) via a syringe. The resulting suspension was stirred overnight, followed by filtration to collect a white solid which was washed with ethanol. The combined filtrate and washing were concentrated leaving a yellow semi-solid residue. The residue was suspended in diethyl ether and filtered to give an off-white solid which was collected and washed with diethyl ether and methylene chloride. The combined filtrate and washings were concentrated to give the title compound as a yellow oil (40.97 g).

Step 4. Preparation of
N-tert-butoxycarbonyl-1-(3-pyridyl)-1-aminopent-4-ene 1-(3-Pyridyl)-1-aminopent-4-ene (24.46 g) was dissolved in dioxane (625 mL) and sodium hydroxide (1N, 500 mL) added. The resulting suspension was cooled in an ice bath and di-tert-butyldicarbonate (102.7 g, 0.661 mol.) in dioxane rapidly added and the reaction mixture allowed to warm to room temperature and stirred overnight. The mixture was evaporated and the resulting residue taken up in water and methylene chloride. The organic layer was separated and set aside and the aqueous layer washed twice with methylene chloride. The organic layers were combined and washed with saturated brine. The washed organic extract was dried over magnesium sulfate, the filtrate dried and concentrated, and the residue purified by flash chromatography over silica gel (eluting with 4:6 ethyl acetate:hexanes). The fractions were combined to yield title compound (64% yield, 25.79 g).

Step 5. Preparation of
N-tert-butoxycarbonyl-1-(3-pyridyl)-1-amino-4,5-dihydroxypentane N-tert-butoxycarbonyl-1-(3-pyridyl)-1-aminopent-4-ene (5.0 g, 0.0191 mol, prepared as described in Step 4) was added to a mixture of osmium tetroxide (5.0 g, 0.0197 mol.) in pyridine. The reaction was stirred at room temperature for 3 hours and then quenched with sodium bisulfite. The solution was stirred at room temperature for 15 minutes and then filtered through Celite. The filter cake was washed with water and the combined filtrate and washings allowed to stand overnight at room temperature. The resulting brown solution was concentrated and purified by flash chromatography on silica gel eluting eith acetone to yield 2.64 g of the title compound (47% yield).

Step 6. Preparation of
N-tert-butoxycarbonyl-1-(3-pyridyl)-1-amino-4-dihydroxy-5-diphenyl-tert-butylsiloxypentane N-tert-butoxycarbonyl-1-(3-pyridyl)-1-amino-4,5-dihydroxypentane (1.0 g, 0.00337 mol., prepared as described in Step 5) was suspended in methylene chloride (8 ml) and triethylamine added. Dimethylaminopyridine (16 mg) in methylene chloride was added and the suspension cooled to −78° C. and tert-butylchlorodiphenylsilane (1.02 g, 0.004 mol) in methylene dichloride added dropwise. The resulting mixture was allowed to warm to room temperature and stirred overnight at room temperature. The reaction mixture was diluted with methylene chloride and washed with citric acid and saturated brine, dried over magnesium sulfate, filtered, and the filtrate concentrated to yield the title compound (1.7 g, 92% yield).

Step 7. Preparation of
4-[N-tert-butoxycarbonyl-1-(3-pyridyl)-1-amino-5-diphenyl-tert-butylsiloxypentanyl]methanesulfonate N-tert-butoxycarbonyl-1-(3-pyridyl)-1-amino-4-dihydroxy-5-diphenyl-tert-butylsiloxypentane (274 mg, 0.0005 mol, prepared as described in Step 6) was dissolved in 2.5 mL methylene chloride and 154 μl triethylamine and cooled to −78° C. Methanesulfonyl chloride (0.001 mol) was added dropwise and the reaction stirred for 45 minutes and diluted with methylene dichloride and washed with ammonium chloride and saturated brine. The washed organic layer was dried over magnesium sulfate, filtered, and the filtrate concentrated under high vacuum yielding title compound (293 mg, 94% yield).

Step 8. Preparation of 1-tert-butoxycarbonyl-2-(3-pyridyl)-5-diphenyl-tert-butylsiloxypyrrolidine.

4-[N-tert-butoxycarbonyl-1-(3-pyridyl)-1-amino-5-diphenyl-tert-butylsiloxypentanyl]methanesulfonate (1.043 g, 0.00167 mol, prepared as described above) was mixed with tetrahydrofuran (10 ml) and potassium tert-butoxide (288 mg, 0.00257) at −78° C. Saturated ammonium chloride and methylene chloride were added after about 30 minutes. After extraction, the organic layer was separated and washed with saturated brine and dried over magnesium sulfate, filtered, and the filtrate concentrated to yield the title compound (747 mg, 87% yield).

Step 9. Preparation of [1-tert-butoxycarbonyl-2-(3-pyridyl)-pyrrolidin-5-yl]methanol.

1-tert-butoxycarbonyl-2-(3-pyridyl)-5-diphenyl-tert-butylsiloxypyrrolidine (165 mg, 0.000319 mol, prepared as described above) was added to tetrahydrofuran (2 ml) and stirred at room temperature under nitrogen atmosphere. Tetra-n-butylammonium fluoride in tetrahydrofuran (0.000479 mol) was added via syringe and the solution stirred at room temperature for 2 hours. The solution was concentrated and the residue taken up in methylene chloride. The resulting solution was washed with ammonium chloride and the aqueous layer washed with methylene chloride. The organic layers were combined, dried over magnesium sulfate, filtered and the filtrate concentrated to a yellow gum. The gum was further purified by flash chromatography on silica gel (eluting with 3:1 ethyl acetate:hexanes) to yield title compound as cis and trans isomers. These isomers were carried on separately through steps 10–12.

Step 10. 1-tert-butoxycarbonyl-2-(3-pyridyl)-pyrrolidin-5-yl]methanol methanesulfonate The 1-tert-butoxycarbonyl-2-(3-pyridyl)-pyrrolidin-5-yl]methanol (50 mg, 0.00018 mol, prepared as in Step 9, above) was added to methylene chloride and stirred under nitrogen atmosphere and cooled to −78° C. Triethylamine (56 μl) was added via syringe, followed by dropwise addition of methanesulfonyl chloride (28 μl). The mixture was stirred for 45 minutes and diluted with methylene chloride and washed with ammonium chloride. The organic layer was dried over magnesium sulfate, filtered, and the filtrate concentrated to yield 69 mg of the title compound as a yellow gum.

Step 11. N-[3-(3,4,5-trimethoxybenzoyl)phenyl]N-(tert-butoxycarbonyl)-[1-(tert-butoxycarbonyl)-2-(3-pyridyl)-pyrrolidin-5-yl]methylamine To a solution of potassium tert-butoxide (33.9 mg, 0.00030 mol) in 1 mL tetrahydrofuran cooled to −78° C. was added a solution of 127.8 mg, 0.00033 mol N-tert-butoxycarbonyl-(3,4,5-trimethoxybenzoyl)aniline (prepared as described in Example 1, Step 7) in 1 mL of tetrahydrofuran. The resulting solution yellow solution was added to a solution of 1-tert-butoxycarbonyl-2-(3-pyridyl)-pyrrolidin-5-yl)methanol methanesulfate (43.1 mg, 0.00012 mol) in 1 mL. The solution was stirred at 60° C. overnight, followed by cooling. The solution was washed with ammonium chloride and brine. The organic extract was dried over magnesium sulfate, filtered, and the filtrate concentrated to a white solid. The solid was purified by flash chromatography on silica gel eluting with 3:7 ethyl acetate:hexanes to yield 34.5 mg (44%) of the title compound.

Step 12. N-[3-(3,4,5-trimethoxybenzoyl)phenyl][2-(3-pyridyl)-pyrrolidin-5-yl]methylamine N-[3-(3,4,5-trimethoxybenzoyl)phenyl]N-(tert-butoxycarbonyl)-[1-(tert-butoxycarbonyl)-2-(3-pyridyl)-pyrrolidin-5-yl]methylamine (70.0 mg, 0.000108 mg, prepared as described above) was stirred with 540 μl of 4M hydrochloric acid and dioxane under nitrogen atmosphere at room temperature. After about 45 minutes, the mixture was concentrated and the residue azeotroped three times with toluene. The resulting yellow solid residue was triturated with ethyl ether and the solid dried overnight under high vacuum to yield 53.8 mg (89%) of the title compound in cis and trans forms. Cis isomer: NMR (CDCl$_3$, 300 MHz): δ1.97–2.09 (c, 1H), 2.55 (bs, 1H), 3.60–3.70 (c, 1H), 3.74–3.84 (c, 1H), 3.85–3.95 (c, 2H), 3.89 (s, 6H), 3.92 (s, 3H), 4.40 (bs, 1H), 5.13 (bs, 1H), 7.07 (s, 2H), 7.12 (d, 2H, J=7.5 Hz), 7.23 (s, 1H), 7.32 (t, 1H, J=9 Hz), 8.07 (bs, 1H), 8.85 (bs, 1H), 9.09 (d, 1H, J=9 Hz), 9.41 (bs, 1H), 10.72 (bs, 1H). Mass Spectrum (DCI/NH$_3$): 448 (M+H)$^+$ Trans isomer: NMR (CDCl$_3$, 300 MHz): δ2.1–2.23 (c, 1H), 2.60 (bs, 3H), 3.55–3.67 (c, 1H), 3.80–3.95 (c, 2H), 3.85 (s, 6H), 3.91 (s, 3H), 4.20 (bs, 1H), 4.41 (bs, 1H), 5.25 (bs, 1H), 7.10 (s, 2H), 7.16 (bs, 1H), 7.23–7.32 (c, 2H), 7.40 (bs, 1H), 7.95 (bs, 1H), 8.89 (bs, 2H), 9.50 (bs, 1H), 10.57 (bs, 1H). Mass Spectrum (FAB): 448 (M+H)$^+$.

EXAMPLE 14

Preparation of N-[2-(3-pyridinyl)thiazolid-4-ylmethyl]-N'-[3-(3,4,5-trimethoxybenzoyl)phenyl]urea

Step 1. Preparation of 2-(3-pyridinyl)-3-tert-butoxycarbonylthiazolid-4-ylmethanol To a solution of 2-(3-pyridinyl)-3-(tert-butoxycarbonyl)-4-thiazolidinecarboxylic acid (4.0 g, prepared as described in Example 1, Step 2) in dry tetrahydrofuran under nitrogen at 0° C. with stirring was added borane dimethylsulfide complex (32 μl of 1M, 2.5 eq.) and the resulting solution was stirred at 0° C. for 2 hours, followed by stirring at room temperature for 16 hours. Methanol (25 mL) was added and the solvents removed by rotoevaporation and the residue partitioned between ethyl acetate and sodium bicarbonate. The aqueous phase was extracted with ethyl acetate and the organic layers washed with saturated aqueous sodium bicarbonate and dried over magnesium sulfate. After filtration the residue was purified by flash chromatography on silica gel eluting with 1:3 hexane:ethyl acetate to yield 1.591 g of the title compound.

NMR (CDCl$_3$, 300 MHz): δ1.26 (bs, 9H), 2.97 (dd, 1H, J=1.5, 12.0), 3.37 (dd, 1H, J=7.0, 12.0), 3.50 (m, 1H), 3.66 (m, 1H), 3.88 (s, 6H), 3.92 (s, 3H), 4.81 (m, 1H), 6.01 (bs, 1H), 6.92 (bd, 1H, J=7.5), 7.06 (s, 1H), 7.18–7.32 (c, 4H), 7.66 (bd, 1H, J=7.5), 8.50 (dd, 1H, J=2.0, 5.5), 8.60 (bs, 1H). IR (CDCl$_3$): 1685, 1580, 1325. Mass Spectrum (DCI/NH$_3$): 566 (M+H)$^+$.

Step 2. Preparation of 2-(3-pyridinyl)-3-tert-butoxycarbonylthiazolid-4-ymethyl methanesulfonate 2-(3-pyridinyl)-3-tert-butoxycarbonylthiazolid-4-ylmethanol (6.7 g, prepared as described in Step 1, above) and triethylamine (4.6 g, 46 mmol) in methylene chloride was reacted with methane sulfonyl chloride (3.4 g) with stirring for 1 hour at 0° C. The reaction mixture was washed with saturated aqueous sodium bicarbonate and brine, dried over magnesium sulfate, filtered and concentrated to title compound (7.9 g)

Step 3. Preparation of 2-(3-pyridinyl)-3-tert-butoxycarbonylthiazolid-4-ylmethylazide The 2-(3-pyridinyl)-3-tert-butoxycarbonylthiazolid-4-ylmethyl methanesulfonate (7.6 g, 1.0 eq., prepared as described in Step 2) and sodium azide (2.6 g, 40 mmol) were dissolved in dimethylformamide and warmed to 105° C. and stirred overnight at the same temperature. The mixture was then cooled to room temperature and washed with brine. The aqueous phase was extracted twice with ethyl acetate. The combined organic layers were washed with brine, dried over magnesium sulfate, filtered and concentrated to 6.5 g of the title compound as a yellow oil. This material was purified by flash chromatography on silica gel (eluting with 1:3 hexanes:ethyl acetate) to give 2.0 g.

Step 4. Preparation of 2-(3-pyridinyl)-3-tert-butoxycarbonylthiazolid-4-ylmethylamine To a solution of 2-(3-pyridinyl)-3-tert-butoxycarbonylthiazolid-4-ylmethylazide (2.0 g, 1.0 eq, prepared as described above.) in methanol was added 1,3-propanedithiol (1.3 g, 2.0 eq.), followed by addition of triethylamine (1.2 g, 12.4 mmol). The reaction was stirred for 4 days at room temperature and then filtered through celite and concentrated. The residue was partitioned between diethyl ether and 10% aqueous hydrochloric acid. The aqueous phase was extracted with diethyl ether and the ether extracts discarded. The aqueous phase was neutralized with solid sodium bicarbonate and extracted three times with chloroform. The combined organic layers were extracted with brine, dried over magnesium sulfate, and concentrated to 1.5 g of title compound as a clear yellow oil.

Step 5. Preparation of 3-(3,4,5-trimethoxybenzoyl)phenylisocyanate 3-(3,4,5-trimethoxybenzoyl)aniline hydrochloride (6.48 g, 1.0 eq., prepared as described in Example 1, Step 8) was suspended in toluene and warmed to reflux. Phosgene gas was bubbled into the reaction mixture until a clear solution was obtained. The reaction mixture was cooled to room temperature and the toluene removed to give an amber-colored liquid which solidified on standing to 0.50 g of the title compound.

Step 6. Preparation of N-[2-(3-pyridinyl)-3-tert-butoxycarbonylthiazolid-4-ylmethyl]N'-[3-(3,4,5-trimethoxybenzoyl)phenyl]urea To a solution of 2-(3-pyridinyl)-3-tert-butoxycarbonylthiazolid-4-ylmethylamine (1.5 mmol, 1.0 eq., prepared as described in step 4, above) dissolved in 5 mL tetrahydrofuran was added 3-(3,4,5-trimethoxybenzoyl)phenylisocyanate (1.5 mmol, 1.0 eq., prepared as described in step 5, above) and the reaction stirred for 1 hour at room temperature. The reaction mixture was poured into aqueous ammonium chloride and extracted twice with ethyl acetate. The combined organic layers were washed with brine, dried over magnesium sulfate, filtered, and concentrated to yield a yellow foam which was purifed by flash chromatography on silica gel eluting with ethyl acetate to give 0.48 g of the title compound as a white foam.

Step 7. Preparation of N-[2-(3-pyridinyl)thiazolid-4-ylmethyl]N'-[3-(3,4,5-trimethoxybenzoyl)phenyl]urea N-[2-(3-pyridinyl)-3-tert-butoxycarbonylthiazolid-4-ylmethyl]N'-[3-(3,4,5-trimethoxybenzoyl)phenyl]urea (0.48 g, prepared as described above) was mixed with a solution of 4M hydrochloric acid and dioxane and stirred for 3 hours at room temperature, the dioxane was removed, and the residue partitioned between ethyl acetate and saturated aqueous sodium bicarbonate. The aqueous phase was extracted with ethyl acetate and the combined organic layers washed with brine, dried over magnesium sulfate, filtered and concentrated. The resulting foam was purified by flash chromatography on silica gel eluting with 5% methanol/chloroform to yield 0.28 g of title compound.

NMR (CDCl$_3$, 300 MHz): $\delta$2.85 (m, 1H), 3.24 (m, 1H), 3.46–3.82 (c, 2H), 3.86 (s, 6H), 3.94 (s, 3H), 5.51 (m, 1H), 5.57 (d, 1H, J=16 Hz), 7.07 (s, 2H), 7.25 (m, 1H), 7.38 (m, 2H), 7.57 (m, 2H), 7.81 (m, 1H), 8.52 (td, 1H, J=6, 1.5 Hz), 8.72 (bs, 1H). Mass Spectrum (DCI/NH$_3$): 509 (M+H)$^+$.

EXAMPLE 15

Preparation of N-[2-(3-pyridinyl)thiazolid-4-ylmethyl]N'-(3-benzoylphenyl)urea dihydrochloride N-[2-(3-pyridinyl)thiazolid-4-ylmethyl]N'-(3-benzoylphenyl)urea dihydrochloride was prepared using the method of Example 14, except 3-benzoylphenylisocyanate was used instead of 3-(3,4,5-trimethoxybenzoyl)phenylisocyanate.

NMR (CDCl$_3$, 300 MHz): $\delta$2.81 (m, 1H), 3.20 (m, 1H), 3.23–3.80 (c, 3H), 5.55 (d, 1H, J=21 Hz), 5.82 (m, 1H), 7.25 (m, 1H), 7.36 (m, 2H), 7.44 (t, 2H, J=7.5 Hz), 7.51–7.86 (c, 7H), 8.49 (m, 1H), 8.72 (s, 1H). Mass Spectrum (DCI/NH$_3$): 419 (M+H)$^+$.

EXAMPLE 16

Preparation of N-[2-(3-pyridinyl)dithiolan-4-ylmethyl]N'-(3-benzoylphenyl)urea

N-[2-(3-pyridinyl)dithiolan-4-ylmethyl]N'-(3-benzoylphenyl)urea was prepared according to the procedure of Example 14, except methyl 2-(3-pyridinyl)-4-dithiolanecarboxylate was used instead of methyl 2-(3-pyridinyl)-3-(tert-butoxycarbonyl)-4-thiazolidinecarboxylate and 3-benzoylphenylisocyanate was used instead of 3-(3,4,5-trimethoxybenzoyl)phenyl isocyanate.

We claim:

1. A compound having the structural formula:

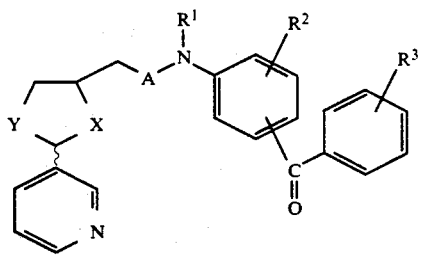

or a pharmaceutically acceptable salt thereof, wherein
R¹ hydrogen or alkyl of from one to six carbon atoms;
R² is one or more groups selected from
hydrogen,
halogen, and
alkyl of from one to six carbon atoms;
R³ is one or more groups selected from
hydrogen,
halogen, and
alkoxy of from one to six carbon atoms;
A is absent or is —N(R⁴)C(O)— where R⁴ is hydrogen or alkyl of from one to six carbon atoms;
X is >NR⁵ where R⁵ is
hydrogen,
alkyl of from one to six carbon atoms,
alkoyl of from one to six carbon atoms,
—C(O)NR⁶R⁷ where R⁶ and R⁷ are independently hydrogen or alkyl of from one to six carbon atoms,
—C(O)OR⁸ where R⁸ is an alkyl radical of from one to six carbon atoms; and
Y is sulfur.

2. A compound as defined by claim 1 having the structure

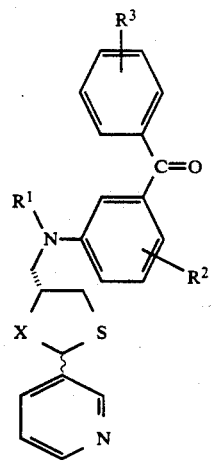

or a pharmaceutically acceptable salt thereof wherein X, R¹, R² and R³ are defined as above.

3. A compound as defined by claim 1 having the structure

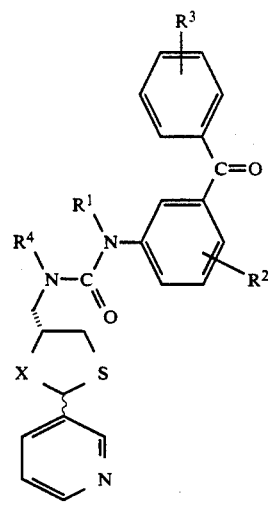

or a pharmaceutically acceptable salt thereof wherein X, R¹, R², R³, and R⁴ are as defined therein.

4. A compound as defined by claim 2 wherein R¹ and R² are independently selected from hydrogen and alkyl of from one to six carbon atoms and R³ is hydogen or alkoxy from one to six carbon atoms, or a pharmaceutically acceptable salt thereof.

5. A compound as defined by claim 4 wherein R¹ is hydrogen or methyl, and R² is hydrogen and and R³ is selected from the group consisting of hydrogen, 3,4 dimethoxy, 3,5-dimethoxy, and 3,4,5-trimethoxy.

6. A compound as defined by claim 3 wherein R¹ and R⁴ are independently selected from hydrogen and alkyl of from one to six carbon atoms; R² is hydrogen; R³ is hydrogen or alkoxy of from one to six carbon atoms; or a pharmaceutically acceptable salt thereof.

7. A compound as defined by claim 6 wherein R¹ and R⁴ are independently selected from hydrogen and methyl; R² is hydrogen, R³ is 3,4,5-trimethoxy, and R⁵ is hydrogen.

8. A compound as defined by claim 1 selected from the group consisting of
N-(3-benzoylphenyl)2-(3-pyridinyl)thiazolid-4-ylmethylamine;
N-(4-benzolyphenyl)2-(3-pyridinyl)thiazolid-4-ylmethylamine;
N-(3-benzoylphenyl)N-methyl2-(3-pyridinyl)thiazolid-4-ylmethylamine;
N-(3-benzoylphenyl)[2-(3-pyridinyl)-3-methylthiazolid-4-yl]methylamine;
N-(3-benzoylphenyl)2-(3-pyridinyl)-3-tert-butoxycarbonylthiazolid-4-ylmethylamine;
N-[3-(3,4,5-trimethoxybenzoylphenyl]2-(3-pyridinyl)-thiazolid-4-ylmethylamine
N-[3-(3,4,5-trimethoxybenzoylphenyl]-[2-(3-pyridinyl)-3-tert-butoxycarbonylthiazolid-4-yl]methylamine;
N-(4-phenoxyphenyl)2-(3-pyridinyl)thiazolid-4-ylmethylamine;
N-[3-(3,4,5-trimethoxybenzoylphenyl]2-(3-pyridinyl)dithiolan-4-ylmethylamine;
N-(3-benzoylphenyl)2-(3-pyridinyl)dithiolan-4-ylmethylamine;
N-[3-(3,4,5-trimethoxybenzoyl)phenyl][2-(3-pyridyl)-pyrrolidin-5-yl]methylamine
N-[2-(3-pyridinyl)thiazolid-4-ylmethyl]-N'-[3-(3,4,5-trimethoxybenzoyl)phenyl]urea;
N-[2-(3-pyridinyl)dithiolan-4-ylmethyl]N'-(3-benzoylphenyl)urea;
or a pharmaceutically acceptable salt thereof.

9. A pharmaceutical composition effective to inhibit platelet-activating factor (PAF) comprising a therapeutically effective amount of a compound as defined by claim 1 in combination with a pharmaceutically acceptable carrier.

* * * * *